US011953346B2

(12) United States Patent
Lee et al.

(10) Patent No.: US 11,953,346 B2
(45) Date of Patent: Apr. 9, 2024

(54) SYSTEM AND METHOD FOR IDENTIFICATION AND ANALYSIS OF CRANIAL CONTOURS

(71) Applicant: LITTLE ANGEL MEDICAL INC., Pointe-Claire (CA)

(72) Inventors: James Lee, Pointe-Claire (CA); Matthew Toews, Pointe-Claire (CA); Tristan Claré, Pointe-Claire (CA)

(73) Assignee: LITTLE ANGEL MEDICAL INC., Pointe-Claire (CA)

(*) Notice: Subject to any disclaimer, the term of this patent is extended or adjusted under 35 U.S.C. 154(b) by 143 days.

(21) Appl. No.: 17/349,909

(22) Filed: Jun. 16, 2021

(65) Prior Publication Data

US 2021/0390708 A1 Dec. 16, 2021
US 2024/0003719 A9 Jan. 4, 2024

Related U.S. Application Data

(60) Provisional application No. 63/039,640, filed on Jun. 16, 2020.

(51) Int. Cl.
*G01D 11/30* (2006.01)
*F16C 1/10* (2006.01)
*F16M 11/06* (2006.01)
*G06T 7/13* (2017.01)
(Continued)

(52) U.S. Cl.
CPC .......... *G01D 11/30* (2013.01); *F16C 1/10* (2013.01); *F16M 11/06* (2013.01); *G06T 7/13* (2017.01); *G06T 7/149* (2017.01); *G16H 50/20* (2018.01); *G06T 2207/20182* (2013.01); *G06T 2207/30016* (2013.01)

(58) Field of Classification Search
CPC .......... G01D 11/30; G06T 7/13; G06T 7/149; G06T 2207/20081; G06T 2207/20084;
(Continued)

(56) References Cited

U.S. PATENT DOCUMENTS

2004/0197016 A1* 10/2004 Littlefield ............. G01N 29/28
382/128
2013/0272588 A1* 10/2013 Luisi ................... G06K 9/00
382/128
(Continued)

FOREIGN PATENT DOCUMENTS

EP 3261056 A1 * 12/2017

OTHER PUBLICATIONS

An Overview of Positional Plagiocephaly and Cranial Remolding Orthoses—2003 (Year: 2003).*
(Continued)

*Primary Examiner* — Nizar N Sivji

(57) ABSTRACT

There is disclosed a system and method for diagnosing plagiocephaly (flat head syndrome, associated primarily with in infants) from photographs of the head. The method and apparatus may involve the use of a processor circuit, for example an application server, for automatically identifying the contour of the head in a plurality of images, then computing geometrical measurements in order quantify plagiocephaly. Photographs are acquired from an overhead view of a head, where the images may be rotated manually or automatically to a standard orientation. For each image, an optimal head contour is identified as minimizing a mathematical cost function combining local image filter responses designed for edge detection and a global model of head contour shape combining smoothness and convexity constrains. Length measurements are then computed from the identified contour, e.g. head diameter, diagonal diameter, and used to quantify the degree of head asymmetry and diagnose plagiocephaly.

10 Claims, 5 Drawing Sheets

(51) Int. Cl.
*G06T 7/149* (2017.01)
*G16H 50/20* (2018.01)

(58) Field of Classification Search
CPC ......... G06T 2207/30004; G06T 7/0016; G06T 7/10; G06T 7/60; G06T 2207/20182; G06T 2207/30016; F16C 1/10; F16C 11/045; F16C 7/00; F16M 11/06; F16M 11/10; F16M 13/00; G16H 50/20
See application file for complete search history.

(56) References Cited

U.S. PATENT DOCUMENTS

| | | | |
|---|---|---|---|
| 2015/0208999 A1* | 7/2015 | Steinfeld | A61B 6/4266 378/205 |
| 2017/0065061 A1* | 3/2017 | McArthur | A45D 44/14 |
| 2018/0042726 A1* | 2/2018 | Yaremchuk | A61B 17/1739 |
| 2021/0004957 A1* | 1/2021 | Aalamifar | G06T 7/10 |
| 2021/0020064 A1* | 1/2021 | Allen | G06T 19/006 |
| 2021/0236080 A1* | 8/2021 | Herrmann | G16H 30/20 |
| 2021/0338194 A1* | 11/2021 | Hsu | G06V 10/25 |

OTHER PUBLICATIONS

Head circumference—a useful single parameter for skull vol. development in cranial growth analysis?—2018 (Year: 2018).*
Three-Dimensional Digital Capture of Head Size in Neonates—A Method Evaluation—2013 (Year: 2013).*
Introducing a new method for classifying skull shape abnormalities related to craniosynostosis—2020 (Year: 2020).*

* cited by examiner

SYSTEM AND METHOD FOR IDENTIFICATION AND ANALYSIS OF CRANIAL CONTOURS

CROSS-REFERENCE TO RELATED APPLICATIONS

This application claims the benefit of U.S. Provisional Patent Application No. 63/039,640 filed on Jun. 16, 2020, which is incorporated by reference herein in its entirety.

FIELD

The present disclosure pertains to a system and method for identification and analysis of cranial contours.

BACKGROUND

Positional plagiocephaly, also referred to as "flat head syndrome", is a condition whereby an infant's head becomes distorted due to pressure on the skull. The condition may be present at birth or develop during the first few months of life as a growing infant's skull is very soft and malleable.

Since the implementation of the "back to sleep" campaign by the American Academy of Pediatrics in the 1990s—which recommended that babies be placed on their back to sleep in order to decrease the risk of sudden infant death syndrome (SIDS)—the incidence of flat head syndrome has increased dramatically, and up to 47% of healthy infants can become affected by positional plagiocephaly. While positional plagiocephaly has not been shown to affect brain development, it can lead to a permanent cosmetic deformity.

In the majority of cases, positional plagiocephaly can be corrected if detected early. Flat head syndrome is typically screened for by pediatricians during routine visits. Diagnosis requires a clinical assessment by examining the infant's head shape. Presently, pediatricians use visual observation and a manual caliper to measure head flatness and assess the severity of the syndrome, if present. However, this manual method of measurement is time consuming, and susceptible to measurement errors.

What is therefore needed is an improved way to identify and analyze cranial contours which addresses at least some of the limitations in the prior art.

SUMMARY

As noted above, the present disclosure relates to a system and method for identification and analysis of cranial contours.

More particularly, the system and method may be used to identify the presence of cranial deformities in infants, and diagnose its severity in order to assess possible treatment options.

In an aspect, there is disclosed a system for automated identification of the head contour of a subject based on an image acquired from an overhead bird's eye view. For example, the image may be acquired by a fixed overhead camera, or a snapshot taken from above with a hand-held mobile phone or camera. This system also includes an algorithm for identifying a stable reference image within a video sequence acquired by a human user.

In an embodiment, the system is configured to identify and detect asymmetry in the cranial contour characteristic of plagiocephaly, and provide a numerical grade of severity of the deformity based on a large number of observations. As positional plagiocephaly has typical patterns and deformities, these patterns may be used to make a clinical diagnosis and recommended treatments, if required. For example, based on a preliminary diagnosis of positional plagiocephaly and a degree of severity, the subject infant may be referred to a physiotherapist, a cranial orthotist, or a specialist (typically a pediatric plastic surgeon or pediatric neurosurgeon) for evaluation.

In certain cases, direct physical measurements of the head may be performed in addition to automated identification and analysis using an acquired image in order to confirm the measurements calculated from an acquired image, and provide for a more accurate and objective diagnosis and better grade the severity of the condition.

In an embodiment, the system is adapted to: receive a set of individual images from a top of an infant subject's head; select an individual image from the set having an accurate representation of the top of the infant subject's head; use the selected individual image for tracing an outline of a contour and a shape of the infant subject's head; identify a position of the infant subject's ears and nose in the traced contour and shape; quantify an asymmetry of the infant subject's head based on the position of the infant subject's ears and nose; and diagnose plagiocephaly based on the quantification of the asymmetry. The position of the ears and nose are identified by specialized detectors, e.g. trained or identifying for blob-like structures around the head contour. The outline is traced with a contour segmentation approach. Advantageously, the system provides a convenient, accurate way to identify and diagnose the severity of positional plagiocephaly in an infant subject by simply acquiring an overhead image of a subject infant's head using a fixed overhead camera, or a mobile phone or other hand-held device.

In another aspect, there is provided a method of automatic identification of the head contour of a subject based on an image acquired from an overhead bird's eye view.

In an embodiment, the method comprises finding a head contour in the image, and then assessing the severity of the asymmetry by measuring various dimensions of the head contour.

In an embodiment, the method comprises acquiring a set of individual images from a top of an infant subject's head; and sending the set of individual images to a computing system having computer-readable medium that stores instructions, which when executed by one or more processors, cause the one or more processors to perform operations comprising: selecting an individual image from the set having an accurate representation of the top of the infant subject's head; detecting the head contour from the selected individual image based on a model of head shape and image gradient operators; quantifying the degree of asymmetry of the infant subject's head based on contour measurements; diagnosing plagiocephaly based on said quantification of the asymmetry.

In this respect, before explaining at least one embodiment of the invention in detail, it is to be understood that the invention is not limited in its application to the details of construction and to the arrangements of the components set forth in the following description or the examples provided therein, or illustrated in the drawings. Therefore, it will be appreciated that a number of variants and modifications can be made without departing from the teachings of the disclosure as a whole. Therefore, the present system, method and apparatus is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

The present system and method will be better understood, and objects of the invention will become apparent, when consideration is given to the following detailed description thereof. Such description makes reference to the annexed drawings, wherein.

DETAILED DESCRIPTION

Figure 1:
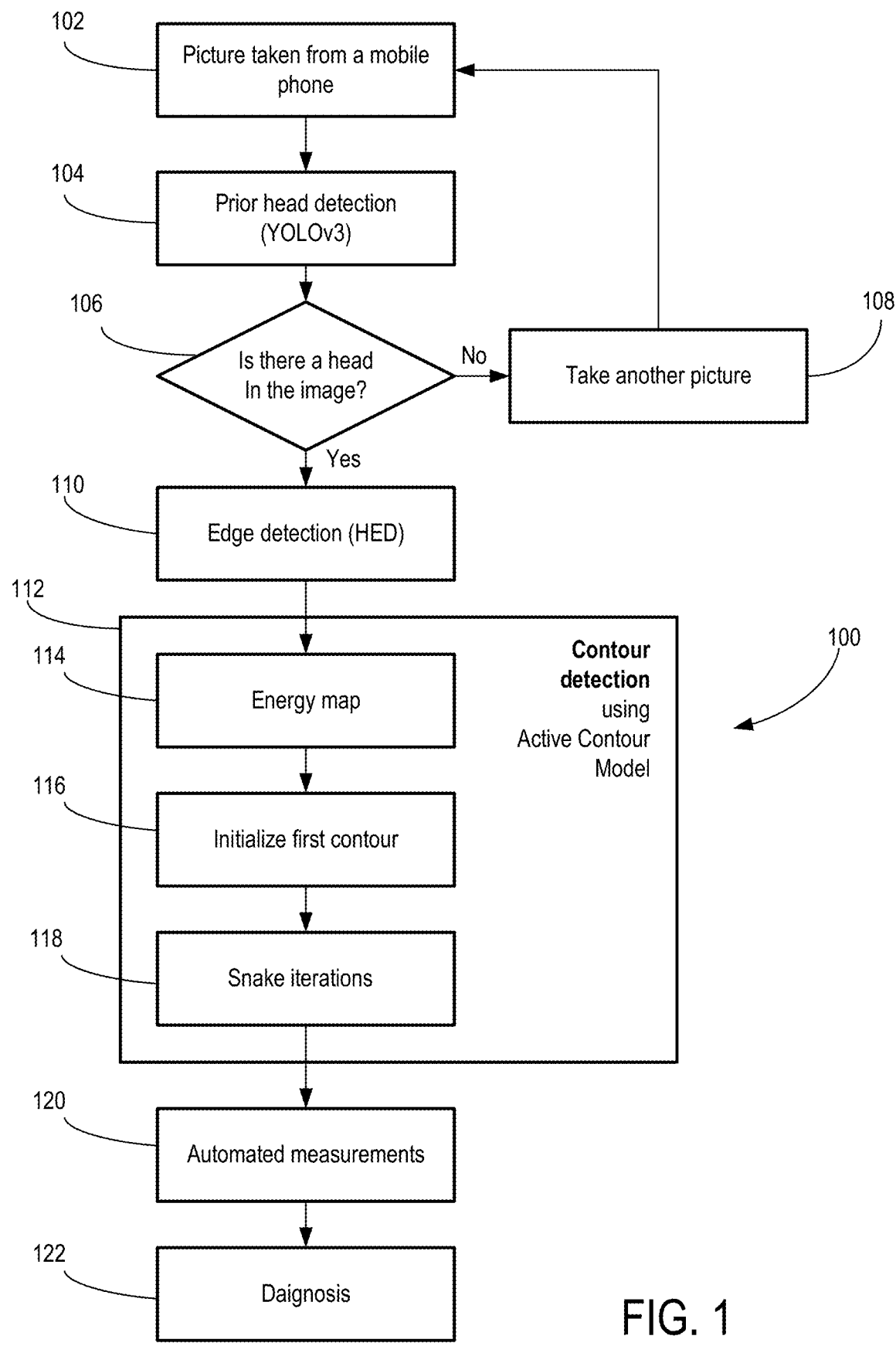
FIG. 1 shows an illustrative method in accordance with an embodiment.

As noted above, the present invention relates to a system and method for identification and analysis of cranial contours.

More particularly, the system and method may be used to identify the presence of cranial deformities in infants, and diagnose its severity in order to assess possible treatment options.

In an aspect, there is disclosed a system for automated identification of the head contour of a subject based on an image acquired from an overhead bird's eye view. For example, the image may be acquired by a fixed overhead camera, or a snapshot taken from above with a hand-held mobile phone or camera.

In an embodiment, the system is configured to identify and detect asymmetry in the cranial contour characteristic of plagiocephaly, and provide a numerical grade of severity of the deformity based on a large number of observations. As positional plagiocephaly has typical patterns and deformities, these patterns may be used to make a clinical diagnosis and recommended treatments, if required. For example, based on a preliminary diagnosis of positional plagiocephaly and a degree of severity, the subject infant may be referred to a physiotherapist, a cranial orthotist, or a specialist (typically a pediatric plastic surgeon or pediatric neurosurgeon) for evaluation.

In certain cases, direct physical measurements of the head may be performed in addition to automated identification and analysis using an acquired image in order to confirm the measurements calculated from an acquired image, and provide for a more accurate and objective diagnosis and better grade the severity of the condition.

In an embodiment, the system is adapted to: receive a set of individual images from a top of an infant subject's head; select an individual image from the set having an accurate representation of the top of the infant subject's head; use the selected individual image for tracing an outline of a contour and a shape of the infant subject's head; identify a position of the infant subject's ears and nose in the traced contour and shape; quantify an asymmetry of the infant subject's head based on the position of the infant subject's ears and nose; and diagnose plagiocephaly based on the quantification of the asymmetry. The position of the ears and nose are identified by specialized detectors, e.g. a trained A.I. for identifying for blob-like structures around the head contour. The outline is traced with a contour segmentation approach.

Advantageously, the system provides a convenient, accurate way to identify and diagnose the severity of positional plagiocephaly in an infant subject by simply acquiring an overhead image of a subject infant's head using a fixed overhead camera, or a mobile phone or other hand-held device.

In another aspect, there is provided a method of automatic identification of the head contour of a subject based on an image acquired from an overhead bird's eye view.

In an embodiment, the method comprises finding a head contour in the image, and then assessing the severity of the asymmetry by measuring various dimensions of the head contour.

In an embodiment, the method comprises acquiring a set of individual images from a top of an infant subject's head; and sending the set of individual images to a computing system having computer-readable medium that stores instructions, which when executed by one or more processors, cause the one or more processors to perform operations comprising: selecting an individual image from the set having an accurate representation of the top of the infant subject's head; detecting the head contour from the selected individual image based on a model of head shape and image gradient operators; quantifying the degree of asymmetry of the infant subject's head based on contour measurements; diagnosing plagiocephaly based on said quantification of the asymmetry.

Illustrative embodiments of the invention will now be described with reference to the drawings.

Several methods have been proposed to assess the shape of the head, the localization of the flatness and the severity of deformational plagiocephaly. Non-imaging based methods are used to quantify the severity of plagiocephaly [9], based on ratios of head measurements acquired directly from the head using calipers. Existing image-based methods involve 3D reconstruction[7] or 3D stereo-photogrammetry [8] to compute a representation of the head shape prior to assessing flatness. The drawback of these methods is the need for specific hardware, the availability of which may be very limited. The main challenges in image-based methods include acquiring data from an infant subject, often in movement, and unexpected noise including hair occlusion of the head contour and background clutter.

Now referring to FIG. 1, shown is an illustrative overview of method 100 in accordance with an embodiment. According to method 100, a picture of a subject is taken, for example from an overhead camera or a mobile phone at block 102.

Figure 2A:
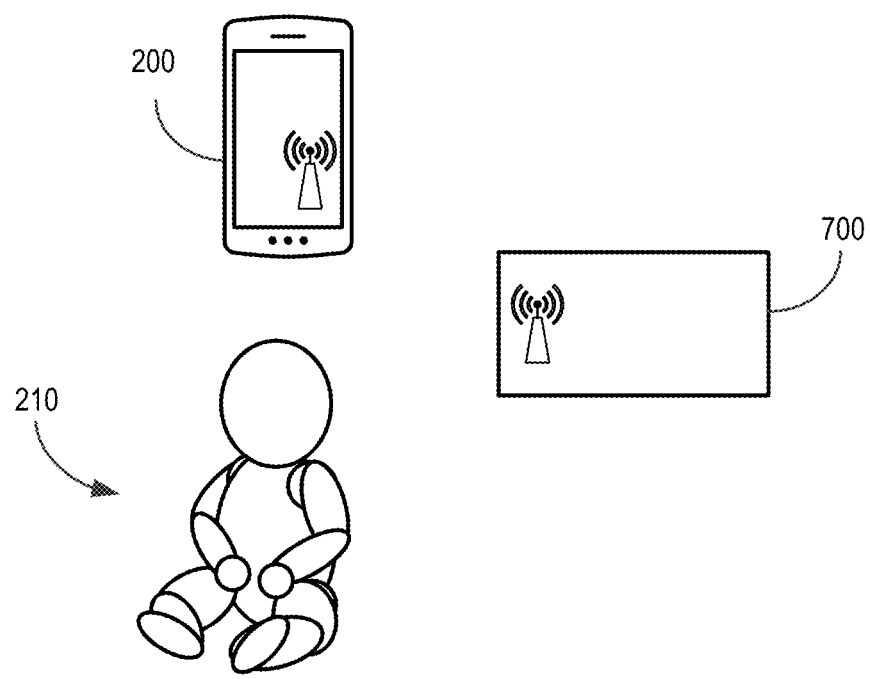
FIG. 2A shows an illustrative system in accordance with an embodiment.
Figure 2B:
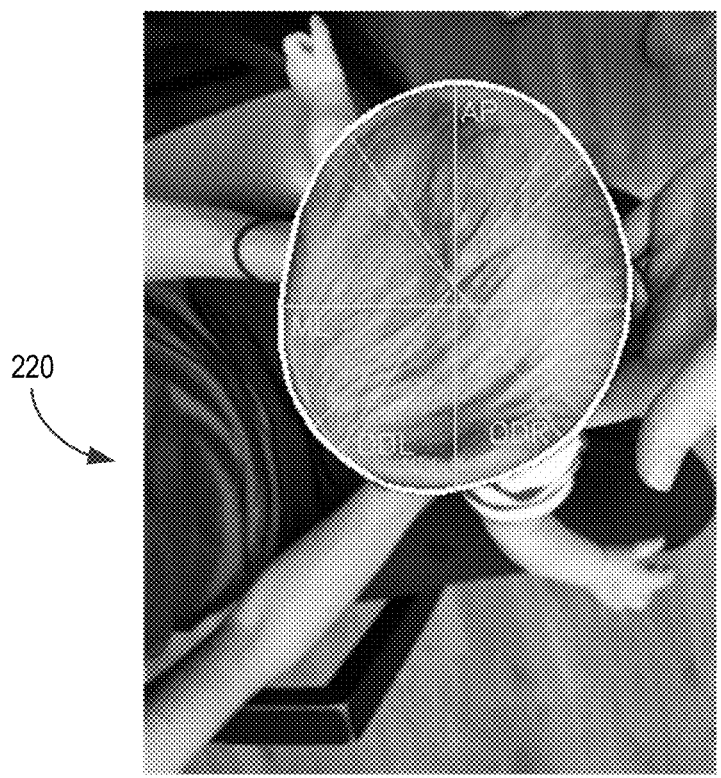
FIG. 2B shows an illustrative acquired image of an overhead view of an infant subject's head with an outlined cranial contour detected within the acquired image.

A system for taking such photos is shown by way of example in FIG. 2A, with a resulting acquired image shown in FIG. 2B. In this illustrative embodiment, data is acquired remotely via standard mobile phone technology, for example, an iPhone™ acquiring an image at 2448 pixels*3264 pixels or another suitable resolution. No additional hardware is needed. Basically, the picture could be captured using any device embedding a camera, including (the following is non-exhaustive):

smart phones, or mobile phones embedding a camera
tablet computers
hand-held digital cameras The image is acquired by holding the smart phone/camera above and pointing downwards towards an infant's head, which is assumed to be positioned approximately in the center of the field of view, and oriented such that the anterior-posterior (AP) axis (i.e. back to font of the head) is oriented generally vertically within the image. In an embodiment, a specialized acquisition view is provided used to guide the user in acquiring the image.

A specialized acquisition view is used to guide the user in acquiring the image. The acquisition view includes a real-time video visualization along with a colored target outline overlayed on the screen, here the outline of a head. The user prompted to aligned the content of interest of the video within the targeted region (here a bird's eye view of the head) according to location, scale and orientation, while a video of the previous 5 seconds is continuously captured. Once the user is satisfied that acceptably alignment has been achieved and maintained over a few seconds, the user presses a stop button indicating capture has been completed.

After acquisition, all input video data are uploaded to a central server (e.g. a computing device 700 of FIG. 7) for subsequent processing. A novel method is used to detect a maximally stable image frame from the input video for analysis via a mobile phone and a user. A video sequence is defined as a function I(x,y,t) mapping space-time coordinates (x,y,t) to a multi-spectral image pixel I. A function D(x,y,t) may be defined in terms of 2nd order partial derivative magnitudes:

$$D(x, y, t) = \left\| \frac{\partial^2 I(x, y, t)}{\partial x^2} + \frac{\partial^2 I(x, y, t)}{\partial y^2} \right\| - k \left\| \frac{\partial^2 I(x, y, t)}{\partial t^2} \right\|$$

where k is a positive constant tuning parameter. D(x,y,t) generalizes the well-known Laplacian operator to account for time $$\left\| \frac{\partial^2 I(x, y, t)}{\partial t^2} \right\|$$

and subtracts the 2nd temporal derivative $$-\left\| \frac{\partial^2 I(x, y, t)}{\partial t^2} \right\|$$

as in the flat space or Minkowski metric in order to identify stable, motion-free image frames, as opposed adding it in order to identify space-time events[12]. D(x,y,t) may be computed for example via finite differences as follows $$D(x,y,t) = \|4I(x,y,t) - I(x-1,y,t) - I(x+1,y,t) - I(x,y-1,t) - I(x,y+1,t)\| - k\|2I(x,y,t) - I(x,y,t-1) - I(x+1,y,t+1)\|.$$

The stable frame of interest is then identified as the time coordinate t_stable where the sum of D(x,y,t) over of spatial coordinates (x,y) is maximized, i.e. with high 2nd order partial derivative magnitude across spatial locations within a single image and low 2nd order partial derivative magnitude between frames.

$$t_{stable} = \underset{t}{argmax} \left\{ \sum_{x}^{Cols} \sum_{y}^{Rows} D(x, y, t) \right\}$$

The image I(x,y,t_stable) at time frame t_stable sent to block 104.

Method 100 then proceeds to block 104, where a head detection step is performed at block 104. As a smart phone user could take any picture, a prior head detection in the image could confirm that the algorithm is not running on something that is not an infant subject's head. In one embodiment, the system and method uses a pre-trained YoloV3 model [10] to detect a person in the image. Alternatively, a more robust detection model may be built by training on a data set of many children images. In an illustrative embodiment, the confidence threshold is set to about 50.0%.

In an embodiment, the acquired image is preprocessed by first subsampling to reduce the image resolution to a fixed dimension, where the smallest dimension (width or height) is scaled, for example, to 300 pixels.

At decision block 106, if a head is not detected in the image, method 100 proceeds to block 108 to take another picture by returning to block 102. If a head is detected in the image, method 100 then proceeds to block 110 in order to perform edge detection of a cranial contour at block 110.

In an embodiment, the acquired image is passed through the trained holistic edge detection (HED) network filters [2] at block 110 in order to generate a robust image map, as a robust alternative to traditional image gradient operators that are susceptible to noise, etc. The HED filter is able to emphasize image structure due to contours of natural 3D objects (such as a head) while avoiding noise and clutter unrelated to object contours (see the output on figure below). The HED filter is a general contour detector, and may be optimized for detecting head contours despite nuisances such as hair from training examples of heads with ground truth.

Method 100 then proceeds to contour detection block 112 where method 100 generates an energy map at block 114.

Method 100 then proceed to block 116 to initialize a first contour prior to applying a Snake algorithm at block 118.

In an embodiment, the head of an infant in an acquired image is assumed to be approximately located in the center of the image. However, the contour must be initialise near the optimal solution in order to ensure convergence, as naïve initialisation will lead to a suboptimal solution. Therefore, at block 116, the contour is initialized based upon an initial head region detection algorithm, whereby a floodfill algorithm is applied to the edge MAP. The flood fill is started from the center image pixel, which is assumed to be located within the head, and identifies a region of dark pixels that contain no edges. A circular initial contour is then generated, where the center of mass (x,y) location of the flooded region is chosen as the contour center, and the radius is defined by the standard deviation of the flooded region. The contour is defined as a sequence of (x,y) image point locations, and the initial contour is defined by a set of points spaced evenly along the perimeter of the circle.

Although one approach is to initialize the contour as a basic centered circle with a given radius, it was observed that if the head was not centered enough in the input image, some points of the initial circle could be positioned outside of the head. Therefore, in an embodiment, the system and method utilizes an HED output to initialize the contour, using a floodfill method. In most cases, the head is completely filled, but sometimes the hair pattern may stop the flooding earlier. However, the result of the floodfill is generally good enough to find an accurate center of the head (more accurate than the center of the image) using the centroid operator. From the flooded area, the system and method also finds an accurate initial radius for the contour. The initial circle is thus created from the new center and radius.

In an embodiment, an optimal head contour is identified by iteratively deforming the initial contour until a set of model constraints is computed from the contour (i.e. list of (x,y) image points) and the Edge Map. In the present illustrative example, the Snake method is adopted, where constraints are formulated as a sum of positive energy functionals, and gradient decent is used to iteratively update the contour points until convergence is achieved at an energy minimum. Specifically, the system and method use the snake method with a balloon force[4][5], where the energy to be minimized is defined as follows:

$$Esnake = Eint + wext \cdot Eext + wbf \cdot Bf \quad (1)$$

The individual terms of Equation (1) are defined below.

Eint is the internal energy of the contour, defined by shape constraints of the contour including continuity and the smoothness of the contour, ensuring a round shape for the head contour. It is defined as:

$$Eint = (\alpha(s)|vs(s)|2 + \beta(s)|vss(s)|2)/2 \quad (2)$$

Where in Equation (2), vs(s) is the first derivative of the contour referred to as the continuity and vss(s) is the contour Laplacian operator (second derivative) known as the curvature, as defined by Kass[4]. $\alpha$ and $\beta$ are empirical parameters given in the table below. Eext is the image energy. The original method proposed by Kass expresses three functionals: line functional, edge functional and termination functional, based on image gradient operators. This method may fail, as these gradient operators are susceptible to image noise, insensitive to weak but relevant contours, and thus causes the algorithm to converge to suboptimal local minima.

To improve robustness the system and method utilizes an image energy using the Edge Map, using the HED edge filters derived via machine learning, thereby emphasize the contour of the head and downweight noise due to hair and random cluster. The HED method produces a bright edge at the head contour, reducing the effect of random noise particularly due to hair. An empirical weight wext is used to control the attraction to the edges. The image energy is defined as:

$$Eext = not(HED2) \quad (3)$$

Bf is the balloon force. The system and method uses this to inflate the contour towards the edges. An empirical weight wbf (see Equation (1) above) is set to increase the balloon force enough to go beyond weak edges; but not too much, so the snake can stick on the real contour.

$$Bf = Ep \quad (4)$$

with Ep the potential energy of the contour, computed from its perimeter, using a normal distribution around an expected perimeter (empirical value=2000). Finally, to ensure that the contour does not go beyond the edges of interest, the system and method utilizes the balloon force with Eext, so that the contour sticks to the edges and does not go beyond.

In an embodiment, a gradient descent algorithm used to iteratively push the initial contour towards and optimal solution, stopping once an energy minimum has been identified.

Method 100 then proceeds to block 120 to perform automated measurements at block 120, and generates a diagnosis at block 122. Method 100 is now described in more detail.

Table 1 below shows illustrative numerical parameters of the snake, where $\gamma$ is the step of the optimization iteration.

TABLE 1

| | |
|---|---|
| $\alpha$ | 0.001 |
| $\beta$ | 0.4 |
| $\gamma$ | 10 |
| iterations | 2500 |
| Number of points in contour | 37 |
| $w_{ext}$ | 0.7 |
| $w_{bf}$ | 2.0 |

Based on van Vlimmeren' paper[9], the system and method assesses the plagiocephaly severity by measuring six lengths: anterior posterior (AP), medium lateral (ML), oblique diameter left (ODL), oblique diameter right (ODR), posterior-ODL (PODL), posterior-ODR (PODR). The scheme below illustrates how the system and method measures it. ML is the widest horizontal length. AP is the vertical-centered length. ODL and ODR intersect AP in its middle, with an angle $\theta$ from AP. Usually $\theta$ is an angle between 30 and 40 degrees, but in the algorithm, the system and method averaged a 35-degree ODL and a 45-degree ODL to get an accurate value of ODL. Same method was used to compute ODR. PODL and PODR are the posterior sections of respectively ODL and ODR.

The system and method then computes two ratios:
CVAI=(max(ODL,ODR)−min(ODL,ODR))/max(ODL, ODR). Four severity levels are defined:

TABLE 2

| | |
|---|---|
| Normal (no plagiocephaly) | 0 ≤ CVAI < 3.5 |
| Mild plagiocephaly | 3.5 ≤ CVAI < 6.25 |
| Moderate plagiocephaly | 6.25 ≤ CVAI < 8.75 |
| Severe plagiocephaly | 8.75 ≤ CVAI |

CR=ML/AP. If CR>0.95, a brachycephaly is diagnosed, otherwise the system and method considers it normal.

If a plagiocephaly is diagnosed (CVAI>3.5), the system and method computes the side from PODL and PODR, the lowest value gives the location of the flatness: left or right. For example, the previous figure is likely a right plagiocephaly, as PODR seems shorter than PODL.

Results

As noted above, FIG. 2B shows an output image of the present system and method with a subject patient head as input.

Two data sets were used to assess the efficiency of the method:
- 22 plaster heads, made by pediatricians from real baby heads who needed custom helmet to correct their plagiocephaly; each one gives two images, the first one is the normal head shape used to make the helmet (A), the second one is the asymmetric head (B), obtained by breaking the plaster extension at the back of the head, which actually is a copy of the real head of the baby
- 16 images of real patients, taken by pediatricians during visits Each head was provided with attached measurements and diagnosis by the pediatrician. In an embodiment, the system and method utilizes this information as the true diagnosis to compare the results with. All the 'true' measurements were performed with a caliper, with a similar method as the one proposed by van Vlimmeren et al. [9].

Figure 3:
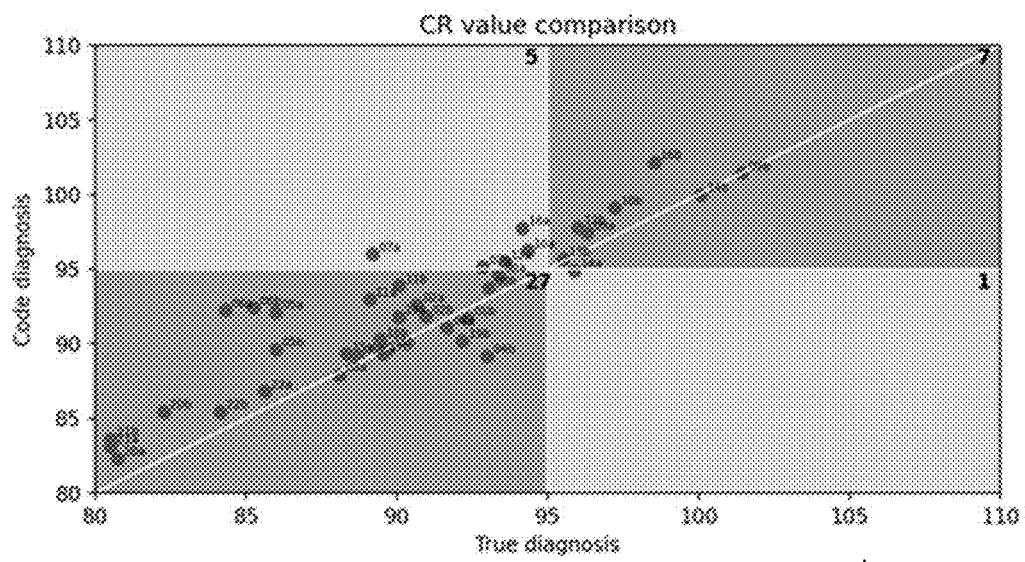
FIG. 3 and FIG. 4 are illustrative graphs showing a CR ratio comparing a true diagnosis and a calculated diagnosis achieved by the present system and method.
Figure 4:
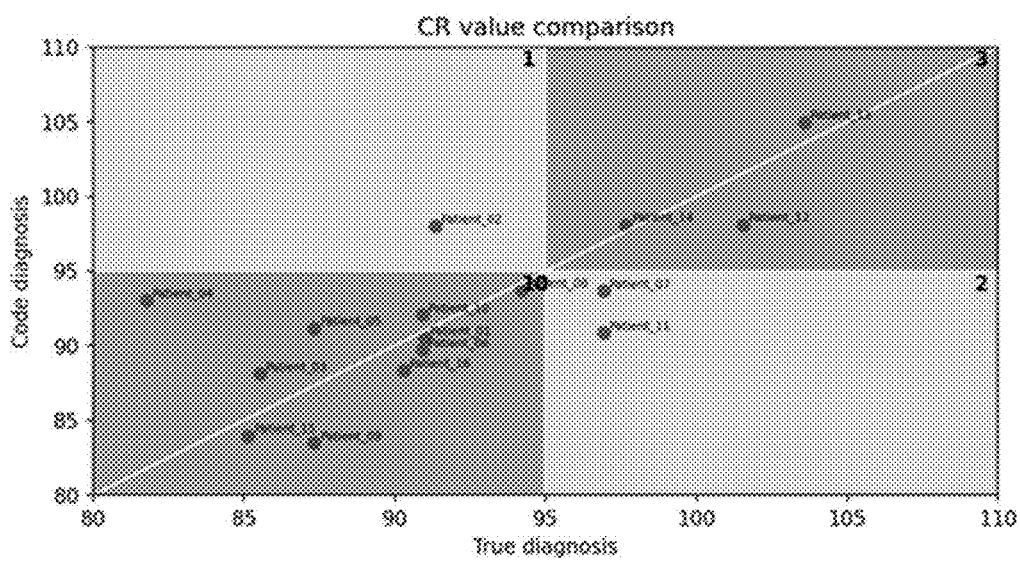
Figure 5:
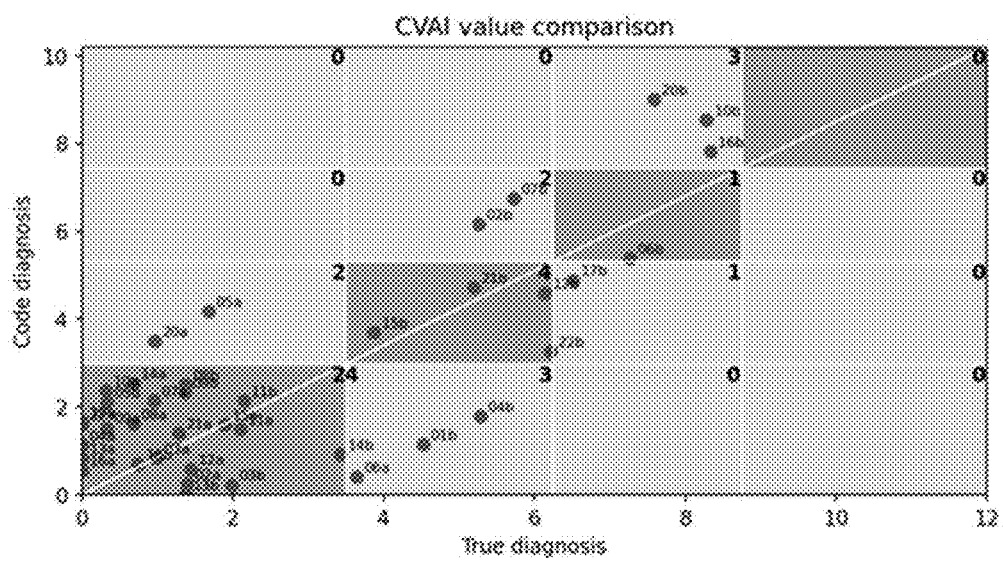
FIG. 5 and FIG. 6 show comparisons of CVAI ratios between a true diagnosis and a calculated diagnosis achieved by the present system and method.
Figure 6:
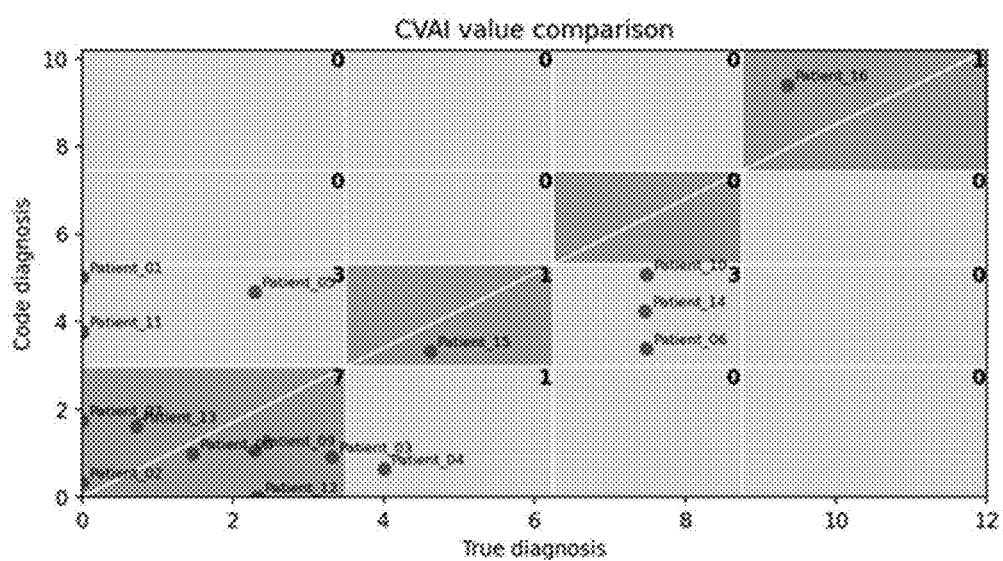

In test trials, the algorithm on both data sets, and the code diagnosis was compared with the true diagnosis. In particular, these trials compared the side of the flatness, the CR, ODDI and CVAI ratios. More particularly, FIG. 3 and FIG. 4 show illustrative graphs showing a CR ratio comparing a true diagnosis and a calculated diagnosis achieved by the present system and method. FIG. 5 and FIG. 6 show comparisons of CVAI ratios between a true diagnosis and a calculated diagnosis achieved by the present system and method.

For all the images, the side (left/right) of the flatness was 100% well assessed. While it is not relevant to bring the side up if the diagnosis is normal. But in all positive cases, the algorithm has proved its robustness to give the right side of the asymmetry.

The graphs below show the CR ratio comparing between the true diagnosis and the result of the algorithm. The vertical and horizontal white lines show the threshold between brachycephaly and normal head. Green areas show correct diagnosis (true positives and true negatives), and red areas shows error.

For the plaster heads, the error rate is 15.0%, while 18.75% for the real patients.

The graphs below show the comparing of CVAI ratios, between true diagnosis and code diagnosis. The diagonal white lines show the thresholds mentioned previously. The error (points in the dark shaded zone) is 27.5% for plaster heads, 43.75% for real heads. The off-by-one error rate is 0.0% in both cases.

The diagnosis thresholds have been altered on the code axis, in order to reduce the error. Thus the new thresholds are 85% the initial thresholds (mentioned previously in this document). Table below gives the adjusted thresholds for the automated diagnosis from the CVAI value.

TABLE 3

| Thresholds | Normal | Mild | Moderate | Severe |
|---|---|---|---|---|
| Normal (true diagnosis) | 0 ≤ CVAI < 3.5 | 3.5 ≤ CVAI < 6.25 | 6.25 ≤ CVAI < 8.75 | 8.75 ≤ CVAI |
| Adjusted (code diagnosis) | 0 ≤ CVAI < 2.98 | 2.98 ≤ CVAI < 5.31 | 5.31 ≤ CVAI < 7.44 | 7.44 ≤ CVAI |

Figure 7:
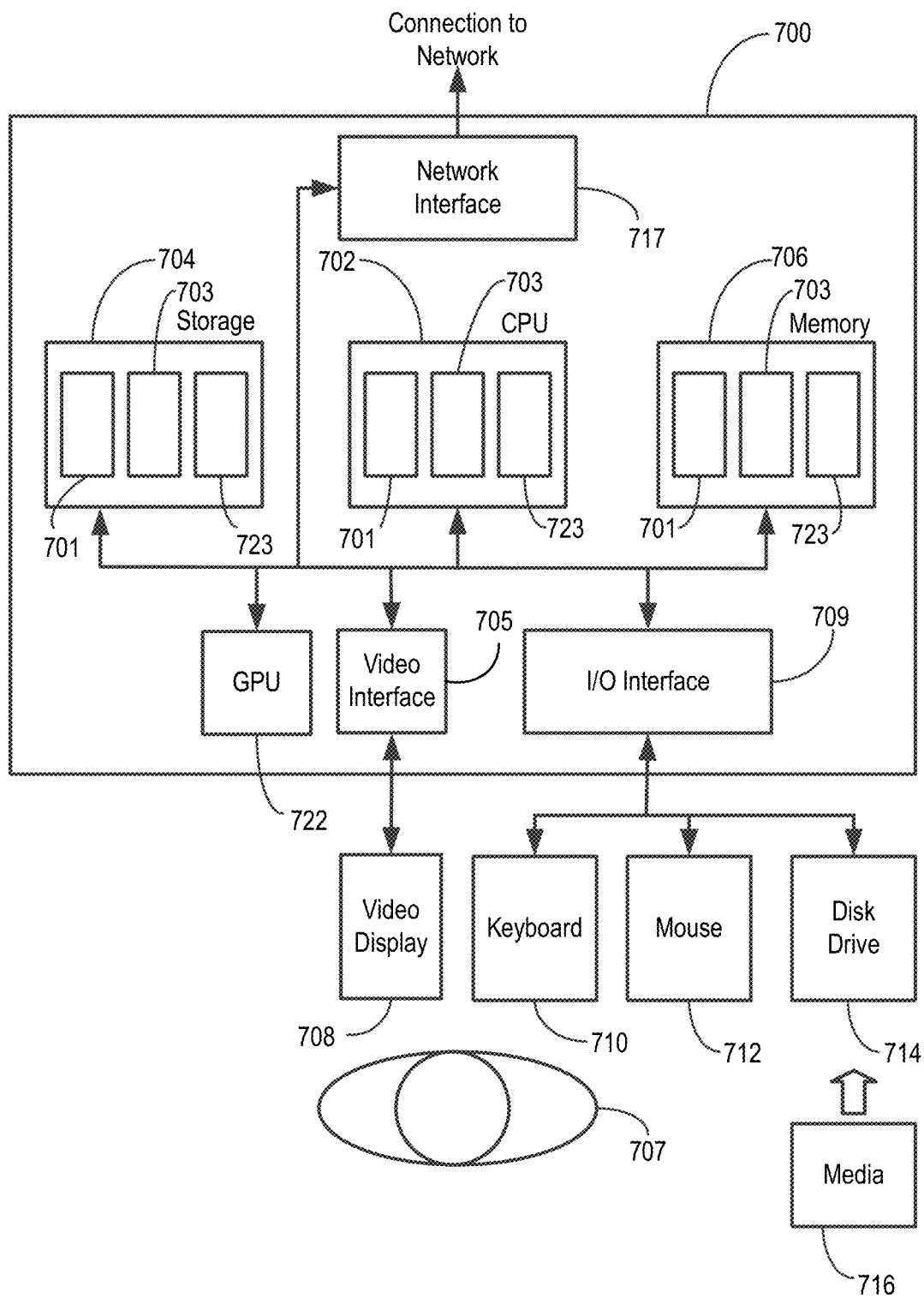
FIG. 7 shows a schematic block diagram of a computing device in accordance with an embodiment.

Now referring to FIG. 7 shown is a schematic block diagram of a computing device that may provide a suitable operating environment in one or more embodiments. A suitably configured computer device, and associated communications networks, devices, software and firmware may provide a platform for enabling one or more embodiments as described above. By way of example, FIG. 7 shows a computer device 700 that may include a central processing unit ("CPU") 702 connected to a storage unit 704 and to a random access memory 706. The CPU 702 may process an operating system 701, application program 703, and data 723. The operating system 701, application program 703, and data 723 may be stored in storage unit 504 and loaded into memory 706, as may be required. Computer device 700 may further include a graphics processing unit (GPU) 722 which is operatively connected to CPU 702 and to memory 706 to offload intensive image processing calculations from CPU 702 and run these calculations in parallel with CPU 702. An operator 710 may interact with the computer device 700 using a video display 708 connected by a video interface 705, and various input/output devices such as a keyboard 710, pointer 712, and storage 714 connected by an I/O interface 709. In known manner, the pointer 712 may be configured to control movement of a cursor or pointer icon in the video display 708, and to operate various graphical user interface (GUI) controls appearing in the video display 708. The computer device 700 may form part of a network via a network interface 717, allowing the computer device 700 to communicate with other suitably configured data processing systems or circuits. A non-transitory medium 716 may be used to store executable code embodying one or more embodiments of the present method on the computing device 700.

Thus, in an aspect, there is provided a system for identifying and analyzing cranial contours, the system adapted to: receive a set of images of a top of an infant subject's head; select an image from the set of images having an accurate representation of the top of the infant subject's head; utilize the selected image for tracing an outline of a cranial contour of the infant subject's head; identify a position of the infant subject's ears and nose in the traced cranial contour to correctly orient the cranial contour; and quantify a degree of asymmetry in the cranial contour.

In an embodiment, the system is further adapted to diagnose plagiocephaly based on the quantification of the asymmetry in the cranial contour.

In another embodiment, the system is adapted to utilize an edge detection method to initialize a cranial contour of the infant subject's head.

In another embodiment, the system is further adapted to utilize a floodfill method to locate a center of the infant subject's head.

In another embodiment, the system is further adapted to find an initial radius for the infant subject's cranial contour.

In another embodiment, the system is further adapted to iteratively update the contour points to identify an optimal cranial contour.

In another embodiment, the system is further adapted to utilize a noise reduction filter to reduce random noise due to hair.

In another embodiment, the system is further adapted to calculate radial distances from the located center of the infant subject's head to specified points on the infant subject's cranial contour.

In another embodiment, the system is further adapted to calculate an assessment of plagiocephaly severity based on the calculated radial distances.

In another embodiment, the system is further adapted to output a diagnosis of plagiocephaly including a level of severity.

In another aspect, there is provided a computer-implemented method of identifying and analyzing cranial contours, comprising: acquiring a set of images from a top of an infant subject's head; selecting an image from the set of images having an accurate representation of the top of the infant subject's head; utilizing the selected image for tracing an outline of a cranial contour of the infant subject's head; identifying a position of the infant subject's ears and nose in the traced cranial contour to correctly orient the cranial contour; and quantifying a degree of asymmetry in the cranial contour.

In an embodiment, the method further comprises diagnosing plagiocephaly based on the quantification of the asymmetry in the cranial contour.

In another embodiment, the method further comprises utilizing an edge detection method to initialize a cranial contour of the infant subject's head.

In another embodiment, the method further comprises utilizing a floodfill method to locate a center of the infant subject's head.

In another embodiment, the method further comprises finding an initial radius for the infant subject's cranial contour.

In another embodiment, the method further comprises iteratively update the contour points to identify an optimal cranial contour.

In another embodiment, the method further comprises utilizing a noise reduction filter to reduce random noise due to hair.

In another embodiment, the method further comprises radial distances from the located center of the infant subject's head to specified points on the infant subject's cranial contour.

In another embodiment, the method further comprises calculating an assessment of plagiocephaly severity based on the calculated radial distances.

In another embodiment, the method further comprises outputting a diagnosis of plagiocephaly including a level of severity.

While illustrative embodiments have been described above by way of example, it will be appreciated that various changes and modifications may be made without departing from the scope of the invention, which is defined by the following claims.

REFERENCES

1: J. Canny, A Computational Approach to Edge Detection, 1986
2: S. Xie, Z. Tu, Holistically-Nested Edge Detection, 2015
3: O. Ronneberger, P. Fischer, T. Brox, U-Net: Convolutional Networks for Biomedical Image Segmentation, 2015
4: M. Kass, A. Witkin, D. Terzopoulos, Snakes: Active Contour Models, 1987
5: L. D. Cohen, On active contour models and balloons, 1991
6: C. Xu, J. L. Prince, Snakes, Shapes, and Gradient Vector Flow, 1998
7: I. Atmosukarto, L. G. Shapiro, M. L. Cunningham & M. Speltz, Automatic 3D Shape Severity Quantification and Localization for Deformational Plagiocephaly, 2009
8: M. Kreutz, B. Fitze, C. Blecher, A. Marcello, R. Simon, R. Cremer, H-F. Zeilhofer, C. Kunz, J. Mayr, Facial asymmetry correction with moulded helmet therapy in infants with deformational skull base plagiocephaly, 2018
9: L. A. van Vlimmeren, T. Takken, L. N. A. van Adrichem, Y. van der Graaf, P. J. M. Helders, R. H. H. Engelbert, Plagiocephalometry: a non-invasive method to quantify asymmetry of the skull; a reliability study, 2005
10: J. Redmon, A. Farhadi, YOLOv3: An Incremental Improvement, 2018
11: S. Ireland-Berk, Fixing a Flat (baby head): What is Plagiocephaly and what can I do to correct it?, https://bdiplayhouse.com/fixing-a-flat-baby-head-what-is-plagiocephaly-and-what-can-i-do-to-correct-it/, 2020
12: Laptev, Ivan. "On space-time interest points." International journal of computer vision 64.2-3 (2005): 107-123.

The invention claimed is:

1. A system for diagnosing and assessing the severity of plagiocephaly based on a quantification of the asymmetry in the cranial contour of an infant subject's head, the system adapted to:
   receive a set of images of a top of an infant subject's head;
   select an image from the set of images having an accurate representation of the top of the infant subject's head;
   utilize the selected image for tracing an outline of a cranial contour of the infant subject's head;
   quantify a degree of asymmetry in the cranial contour;
   locate a center of the infant subject's head to find an initial radius for the infant subject's cranial contour;
   identify an optimal cranial contour by iteratively updating the contour points;
   calculate radial distances from the located center of the infant subject's head to specified points on the infant subject's cranial contour;
   calculate an assessment of plagiocephaly severity based on the calculated radial distances; and
   output a diagnosis of plagiocephaly including a level of severity.

2. The system of claim 1, wherein the system is adapted to utilize an edge detection method to initialize a cranial contour of the infant subject's head.

3. The system of claim 1, wherein the system is adapted to utilize a floodfill method to locate the center of the infant subject's head.

4. The system of claim 1, wherein the system is further adapted to utilize a noise reduction filter to reduce random noise due to hair.

5. The system of claim 1, wherein the cranial contour is correctly oriented by identifying a position of the infant subject's ears and nose in the traced cranial contour.

6. A computer-implemented method for diagnosing and assessing the severity of plagiocephaly based on a quantification of the asymmetry in the cranial contour of an infant subject's head, comprising:
   acquiring a set of images from a top of an infant subject's head;
   selecting an image from the set of images having an accurate representation of the top of the infant subject's head;
   utilizing the selected image for tracing an outline of a cranial contour of the infant subject's head;
   quantifying a degree of asymmetry in the cranial contour;
   locating a center of the infant subject's head to find an initial radius for the infant subject's cranial contour;
   identifying an optimal cranial contour by iteratively updating the contour points;
   calculating radial distances from the located center of the infant subject's head to specified points on the infant subject's cranial contour;
   calculating an assessment of plagiocephaly severity based on the calculated radial distances; and
   outputting a diagnosis of plagiocephaly including a level of severity.

7. The method of claim 6, further comprising utilizing an edge detection method to initialize a cranial contour of the infant subject's head.

8. The method of claim 6, further comprising utilizing a floodfill method to locate a center of the infant subject's head.

9. The method of claim 6, further comprising utilizing a noise reduction filter to reduce random noise due to hair.

10. The method of claim 6, wherein the cranial contour is correctly oriented by identifying a position of the infant subject's ears and nose in the traced cranial contour.

* * * * *